US008434349B2

(12) United States Patent
Blomberg et al.

(10) Patent No.: US 8,434,349 B2
(45) Date of Patent: May 7, 2013

(54) METHOD OF ANALYSING THE HYDROCARBON COMPOUNDS IN A BITUMINOUS MATERIAL

(75) Inventors: Jan Blomberg, Amsterdam (NL); Patricia Le Coutaller, Petit Couronne (FR); François Julien Raoul Deygout, Petit Couronne (FR)

(73) Assignee: Shell Oil Company, Houston, TX (US)

( * ) Notice: Subject to any disclaimer, the term of this patent is extended or adjusted under 35 U.S.C. 154(b) by 730 days.

(21) Appl. No.: 12/529,741

(22) PCT Filed: Mar. 7, 2008

(86) PCT No.: PCT/EP2008/052751
§ 371 (c)(1),
(2), (4) Date: Feb. 23, 2010

(87) PCT Pub. No.: WO2008/107477
PCT Pub. Date: Sep. 12, 2008

(65) Prior Publication Data
US 2010/0139367 A1    Jun. 10, 2010

(30) Foreign Application Priority Data

Mar. 7, 2007  (EP) .................................. 07290300

(51) Int. Cl.
*G01N 30/16*  (2006.01)
(52) U.S. Cl.
USPC ....................................................... 73/23.41
(58) Field of Classification Search ............... 73/23.35, 73/23.41
See application file for complete search history.

(56) References Cited

U.S. PATENT DOCUMENTS

| | | | |
|---|---|---|---|
| 4,394,263 A | 7/1983 | Dosch et al. | |
| 4,469,601 A | 9/1984 | Beaver et al. | |
| 4,990,456 A * | 2/1991 | Loucks et al. | 436/139 |
| 5,132,225 A * | 7/1992 | Dickakian | 436/60 |
| 5,135,549 A | 8/1992 | Phillips et al. | |
| 5,196,039 A | 3/1993 | Phillips et al. | |
| 5,398,539 A | 3/1995 | Gordon et al. | |
| 6,007,602 A | 12/1999 | Ledford, Jr. et al. | |
| 6,547,852 B2 | 4/2003 | Ledford, Jr. et al. | |
| 6,679,941 B2 * | 1/2004 | Van Der Horst et al. | 106/284.01 |
| 7,875,464 B2 * | 1/2011 | Schabron et al. | 436/181 |

(Continued)

FOREIGN PATENT DOCUMENTS

| | | |
|---|---|---|
| EP | 0400989 | 12/1990 |
| SU | 463067 | * 3/1975 |
| WO | WO2007071634 | 6/2007 |

OTHER PUBLICATIONS

Schoenmakers P J et al: "Comparison of comprehensive two-dimensional gas chromatography and gas chromatography—mass spectrometry for the characterization of complex hydrocarbon mixtures", Journal of Chromatography, vol. 892, No. 1-2, Sep. 15, 2000, pp. 29-43.

(Continued)

*Primary Examiner* — Daniel Larkin
(74) *Attorney, Agent, or Firm* — Charles W. Stewart

(57) ABSTRACT

A method of analysing the hydrocarbon compounds in a bituminous material by means of comprehensive multi-dimensional gas chromatography is disclosed. The method may be used to measure the quantity of polycyclic aromatic compounds (PACs) in a bituminous material and may be used to determine the mutagenic tendency of a bituminous material.

20 Claims, 2 Drawing Sheets

U.S. PATENT DOCUMENTS

| | | |
|---|---|---|
| 2003/0100124 A1 | 5/2003 | Beens |
| 2005/0106743 A1 | 5/2005 | Zilioli et al. |
| 2005/0139076 A1 | 6/2005 | Ledford, Jr. |
| 2007/0137481 A1* | 6/2007 | Blomberg et al. ............... 95/82 |

OTHER PUBLICATIONS

H.C.A. Brandt, P.C. De Groot, J. Blomberg: "Development of an Analytical Marker for the Prediction of Biological Activity of Bitumen Fumes and Bitumens Using the FIA-DMSO Set-Up. Experimental Set-Up and Correlation with Mutagenicity and Carcinogenicity" Polycyclic Aromatic Compounds, vol. 16, No. 1-4, 1999, pp. 21-29.

Diehl J W et al: "Determination of aromatic hydrocarbons in gasolines by flow modulated comprehensive two-dimensional gas chromatography". Journal of Chromatography A, vol. 1080, No. 2, Jul. 8, 2005, pp. 157-165.

Blomberg, J. et al., Characterization of Complex Hydrocarbon Mixtures using On-Line Coupling of Size-Exclusion Chromatography and Normal-Phase Liquid Chromatography to High-Resolution Gas Chromatography, Journal of High Resolution Chromatography, vol. 20, Mar. 1997, pp. 125-130.

van Mispelaar, V.G. et al., "Quantitative Analysis of Target Components by Comprehensive Two-Dimensional Gas Chromatograpny", Journal of Chromatography A, vol. 1019, 2003, pp. 15-29.

* cited by examiner

METHOD OF ANALYSING THE HYDROCARBON COMPOUNDS IN A BITUMINOUS MATERIAL

The present application claims priority from European Patent Application 07290300.8 filed 7 Mar. 2007.

FIELD OF THE INVENTION

The invention is directed to a method of analysing the hydrocarbon compounds in a bituminous material.

BACKGROUND OF THE INVENTION

Bitumen is a complex mixture of hydrocarbons and hydrocarbon derivatives, including aliphatic, naphthenic and aromatic compounds. The components in bitumen are conventionally classified using four broad component groups: asphaltenes, resins, aromatics and saturates. Asphaltenes are black or brown amorphous solids and are generally considered as highly polar and complex aromatic materials of fairly high molecular weight. Resins are dark brown in colour, solid or semi-solid and very polar in nature. Aromatics are dark brown viscous liquids and typically consist of non-polar carbon chains in which unsaturated ring systems dominate. Saturates are non-polar viscous oils which are straw or white in colour and comprise aliphatic hydrocarbons together with alkyl-naphthenes and some alkyl-aromatics.

Characterisation of the compounds in a bituminous material is typically carried out by extracting the required fraction with a solvent, separating the required compounds from this fraction (using e.g. liquid chromatography) and analysing the separated compounds (using e.g. gas chromatography). Techniques of this type can be used to analyse the saturates, aromatics and resins in a bitumen (the asphaltenes cannot generally be extracted with a solvent and are precipitated using a short alkane such as heptane), but the techniques are complex and time-consuming. Also consecutive solvent extractions and evaporations lead to loss of more volatile compounds in the bituminous material, decreasing the efficacy of the characterisation. The present inventors have sought to provide a simple and effective method of analysing the components that are present in bituminous materials.

Bituminous materials may contain trace amounts of polycyclic aromatic compounds (PACs). During handling of bituminous materials at elevated temperatures (e.g. during road paving or roofing) fumes are emitted that may contain traces of PACs. Although PAC concentrations are small, worker exposure to bitumen fumes is of potential concern because some PACs are considered to be carcinogenic. Brandt et al, in *Polycyclic Aromatic Compounds* 16 (1999) 21, describe a method of measuring the quantity of PACs in bituminous materials. A sample is subjected to solvent extraction using dimethylsulfoxide in a Flow Injection Analysis coil. The extraction is followed by normal phase liquid chromatography and then gas chromatography. This method is effective but complex. The present inventors have sought to provide a simpler method of analysing bituminous materials that permits the determination of the quantity of PACs.

SUMMARY OF THE INVENTION

Accordingly, the present invention provides a method of analysing the hydrocarbon compounds in a bituminous material by means of comprehensive multi-dimensional gas chromatography, comprising steps of (a) deasphalting a sample of the bituminous material, thereby providing a deasphalted sample;
(b) adding a solvent to the deasphalted sample, thereby providing a dissolved sample;
(c) using a programmed temperature vaporiser to inject the dissolved sample into a first capillary column, wherein the first capillary column comprises a non-polar stationary phase, thereby providing a first separated stream that emerges from the first capillary column;
(d) subjecting the first separated stream to a thermal modulation, thereby providing a thermally modulated stream;
(e) supplying the thermally modulated stream to a second column comprising a polar stationary phase, thereby providing a second separated stream that emerges from the second capillary column; and
(f) analysing the components in the second separated stream.

DETAILED DESCRIPTION OF THE INVENTION

Figure 1:
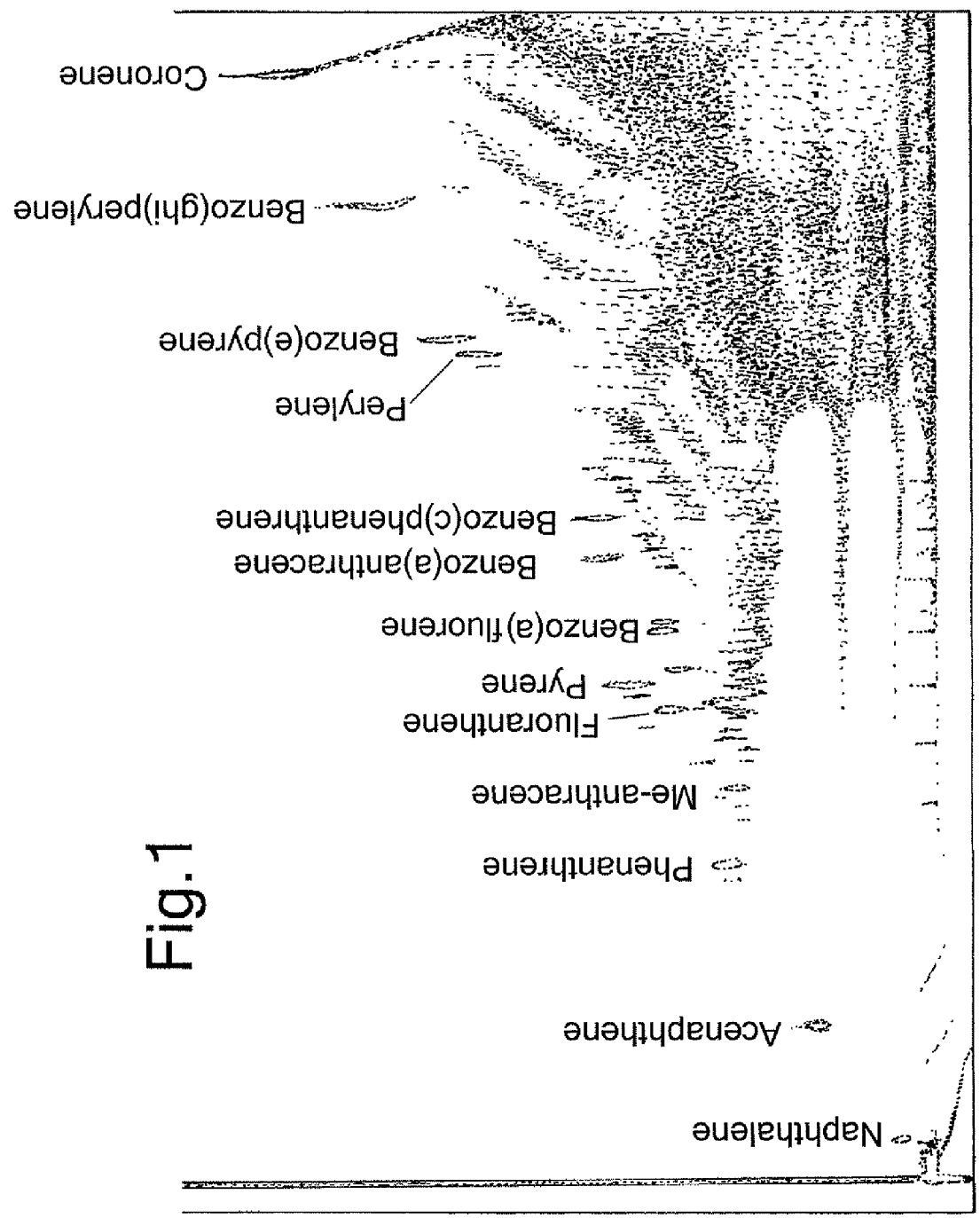
FIGS. 1 and 2 show greyscale two-dimension plots resulting from a method of analysing a bituminous material according to the invention.

Comprehensive two-dimensional gas chromatography (GCxGC) is a well known analytical method and is for example described by Blomberg et al in *Journal of High Resolution Chromatography* 20 (1997) 125 and in Schoenmakers et al, *Journal of Chromatography A* 892 (2000) 29. GCxGC techniques have not previously been applied in the analysis of bituminous materials. Commercial GCxGC equipment and techniques are typically designed to analyse compounds that have boiling points up to 300° C. Many of the hydrocarbon compounds of interest in bitumen having boiling points higher than 300° C. and the known techniques cannot reliably analyse these compounds. The present inventors have devised a modified GCxGC technique that permits reliable analysis of the hydrocarbon compounds in a bituminous material and allows re-use of the GCxGC equipment for numerous analyses. Results obtained by the method of the present invention were presented at the Meeting of the International Society for Polycyclic Aromatic Compounds in Toronto, Canada in 2005, but the specific steps of the experimental method used to obtain the results were not disclosed.

Deasphalting the sample of the bituminous material removes the asphaltenes from the bituminous material. It is necessary to deasphalt the bituminous material before it is supplied to the capillary columns of the gas chromatograph because the asphaltenes can lead to fouling of the columns. Additionally, removal of the asphaltenes makes it easier to dissolve the sample prior to supply to the gas chromatograph. Hydrocarbon solvents, for example heptane and pentane, are typically used to deasphalt the sample of bituminous material. Preferably, pentane is used because it removes a greater quantity of asphaltenes and therefore the risk of fouling of the capillary columns is less.

In a typical deasphalting procedure, a sample of bituminous material is dissolved in a solvent such as toluene. A suspension is prepared by adding a solvent such as pentane, stirring and leaving for a short period, e.g. 30 minutes. The suspension is filtered and the pentane is evaporated from the filtrate, e.g. by heating and application of a stream of nitrogen.

The solvent that is added to the deasphalted sample is preferably cyclohexane or carbon disulphide, most preferably cyclohexane. Preferably the amount of solvent is just sufficient to dissolve the deasphalted sample. Typically the ratio of solvent to dissolved sample is from 0.5-10 ml/g, preferably from 1-5 ml/g.

A programmed temperature vaporizer (PTV) is a sample introduction device used in gas chromatography. The dissolved sample is introduced, typically with a syringe, into the PTV, when the temperature of the PTV is lower than the boiling points of the compounds in the bituminous material. The PTV is then heated very rapidly in a controlled fashion to evaporate the dissolved sample into a continuously flowing carrier gas stream which enters the first column. If the hydrocarbon compounds of interest in the bituminous sample are present in small or very small quantities (e.g. if it is desired to measure the quantity of PACs in the bituminous material) the PTV is preferably used in split mode wherein carrier gas stream is split into two portions, one of which is conducted into the first column while the other is discarded. Alternatively the PTV may be used in a solvent vent mode as this enables quantities of the solvent to be vented before analysis and thereby concentrates the hydrocarbon compounds that are to be analysed.

Preferably the sample is injected into the PTV using a syringe equipped with a metal plunger and not a polytetrafluoroethylene (PTFE)-tipped plunger because the bituminous material can accumulate in a PTFE-tipped syringe and block the syringe. Even with a metal plunger it is preferred to rinse the syringe after each injection. Preferably a support material, e.g. quartz wool, is present in the PTV. Most preferably the quartz wool is not compacted and is present up to approximately 1.5 cm from the top of the liner in the PTV. During injection of the dissolved sample it is preferred that the syringe actually touches the quartz wool.

The first capillary column comprises a non-polar stationary phase and the components from the bituminous material are separated according to boiling point. Therefore the first separated stream that emerges from the first capillary column comprises components separated by boiling point. The non-polar stationary phase in the first capillary column is preferably a substituted polysiloxane stationary phase, most preferably a dimethyl-polysiloxane stationary phase (in this technical field this is also referred to as pure dimethyl-polysiloxane). Such first capillary columns are commercially available, for example as DB-1 from J&W Scientific, Folsom, Calif., USA.

The length of the first column is preferably between 5 and 50 m, more preferably between 8 and 12 m, the internal diameter of the first column is preferably between 0.1 and 0.6 mm, more preferably between 0.2 and 0.3 mm and the thickness of the stationary phase is preferably between 0.05 and 3 µm. The preferred length of the column will be influenced by the thickness of the stationary phase. The dimensions of the column are chosen to provide sufficient separation of the bituminous components of interest by boiling point. The separation of the column can be checked using a reference sample of hydrocarbon compounds, e.g. if it is desired to analyse the PAC content of the bituminous material then a calibration sample of PACs can be used.

The first separated stream is subjected to a thermal modulation, thereby providing a thermally modulated stream. The thermal modulation comprises alternately trapping and releasing compounds. The principle and apparatus for performing such a thermal modulation is for example described in U.S. Pat. No. 5,135,549. In this patent publication a moving heat source runs along a section of column to release accumulated compounds into the second column. More preferably modulation is being achieved by means of alternating cooling and heating. Preferably such thermal modulation is performed making use of a so-called cryogenic modulator or a two-jet cryogenic modulator as for example described in U.S. Pat. No. 6,547,852 and US-A-2005/0139076. Other possible modulators and apparatus to perform the comprehensive multi-dimensional gas chromatography according to the present invention are described in US-A-2003/0100124 and in US-A-2005/0106743.

In a preferred method, the modulation comprises a heating period of 400 ms every 10000 ms. This can be achieved with a two-jet cryogenic modulator having a continuous cold jet (liquid nitrogen) and a hot jet (nitrogen gas) that pulses for 400 ms every 10000 ms.

The first separated stream is preferably subjected to thermal modulation in an additional capillary column. The capillary column is preferably a diphenyltetramethyl-disilazane (DPTMDS) deactivated fused silica capillary column. The length of the column is preferably between 0.5 and 4 m and the internal diameter of the second column is preferably between 0.01 and 0.6 mm.

The second capillary column comprises a polar stationary phase and the components from the bituminous material are separated according to polarity. Therefore the second separated stream that emerges from the second capillary column comprises components that have been separated by boiling point and by polarity. The second capillary column is preferably a polysilphenylene-siloxane stationary phase most preferably a 50% phenyl (equivalent) polysilphenylene-siloxane stationary phase. The term equivalent refers to the fact that phenyl groups form part of the backbone of the siloxane polymer. This stationary phase is well known and columns containing said phase are, for example, the BPX50 as obtainable from SGE, Ringwood, Australia.

The length of the second column is preferably between 0.5 and 1.5 m, the internal diameter of the second column is preferably between 0.05 and 0.2 mm and the thickness of the stationary phase is preferably between 0.01 and 0.2 µm. The preferred length of the column will be influenced by the thickness of the stationary phase. The dimensions of the column are chosen to provide sufficient separation of the bituminous components of interest by polarity. The separation of the column can be checked by using a hydrocarbon reference sample, e.g. if it is desired to analyse the PAC content of the bituminous material then a calibration sample of PACs can be used.

The components in the second separated stream are typically analysed by passing the stream through another capillary column, preferably a DPTMDS deactivated fused silica capillary column, prior to a flame ionisation detector. The length of the column is preferably between 0.05 and 1 m and the internal diameter of the column is preferably between 0.01 and 0.6 mm. The characteristics and operation of flame ionisation detectors are well known to the person skilled in the art.

It is important that the columns are connected so that leaks between columns are minimised and dead volume between columns is minimised. Dead volume can lead to peak widening and a loss of resolution in the GCxGC chromatograms. Preferably metal connectors are used to connect the columns (quartz can dilate at temperatures above 270° C. thereby causing leaks). Preferred connectors include SilTite™ mini unions available from SGE Analytical Science Pty Ltd.

In the first column the compounds in the sample are separated according to their different boiling points. The first separated stream from the first column comprises separated components that are accumulated and concentrated by the thermal modulation to form a thermally modulated stream comprising small packages of components which are subsequently released at frequent intervals into the second-dimension column. Since the separation in the second column is much faster than the separation in the first column, several second-dimension separations can be developed over a single separation of the first dimension. As a consequence, the separation performed by the first column can essentially be maintained. Separation of the sample on independent (orthogonal) component properties (volatility and polarity), results in an ordered separation and effective use of the high peak capacity of the two-dimensional space. The sample elutes entirely and information on a molecular level can be obtained over a large boiling-range.

The results of comprehensive multi-dimensional gas chromatograms are usually presented as false-colour plots in which full-range bands of the different hydrocarbon group-types appear. Every band can be divided up in 'tiles' that represent the hydrocarbon group of a given carbon number (isomers). Within each tile, there is an ordering based on the branching of the alkyl-substitutents. Since increased branching apparently also leads to a reduced polarity, a tile displays a certain inclination in the chromatogram. As a result, different tiles are stacked in the increasing direction of the first dimension, commonly denoted as 'roof-tiling'.

Polycyclic aromatic compounds (PACs) are arranged in a chromatogram according to boiling point in the first dimension and according to polarity (number of aromatic rings) in the second dimension. Concentrations of PACs are indicated through false-colour display of the detector-signal intensity. PAC isomers are grouped in roof-tile like clusters and after integration, the concentrations of the different PAC groups can be determined.

The present invention further provides a method of measuring the quantity of polycyclic aromatic compounds (PACs) in a bituminous material using a method of analysis according to the invention.

As described by Brandt et al, in *Polycyclic Aromatic Compounds* 16 (1999) 21, it is possible to correlate the PAC concentration of a bituminous material with its mutagenic tendency. Therefore, the present invention further provides a method of determining the mutagenic tendency of a bituminous material by measuring the quantity of PACs by a method according to the invention.

The invention will now be described by reference to an example which is not intended to be limiting of the invention.

EXAMPLE

The samples were analyzed using an Agilent 6890 GC (Agilent Technologies, Avondale, Pa., USA) equipped with a Gerstel CIS-4 PTV injector (Gerstel GmbH & Co. KG, Mülheim an der Ruhr, Germany), a CTC-PAL multi-purpose sampler (CTC Analytics AG, Zwingen, Switzerland) and a flame ionisation detector. The system was fitted with a loop-type liquid-nitrogen cryogenic thermal modulator (ZOEX Corporation, Lincoln, Nebr., USA) set to a modulation time of 10 seconds and equipped with a second dimension-column oven (ZOEX), enabling independent second-dimension column heating.

The first dimension column consisted of a 10 m length×250 µm internal diameter DB-1 column with a film thickness of 0.10 µm (100% dimenthylpolysiloxane, J&W Scientific Inc., Folsom, Calif., USA). The capillary column for temperature modulation consisted of a 2 m length×0.10 mm internal diameter diphenyltetramethyl-disilazane (DPTMDS) deactivated fused silica capillary (BGB Analytik, Anwil, Switzerland). The second dimension column consisted of a 0.8 m length× 0.10 mm internal diameter BPX50 column with a film thickness of 0.05 µm (50% equiv. Polysilphenylene siloxane, SGE, Ringwood, Australia). A DPTMDS deactivated fused silica capillary column (BGB Analytik, Anwil, Switzerland) with a length of ~0.2 m and an internal diameter of 0.10 mm was used to connect the second dimension column to the flame-ionization detector (FID). Columns were coupled with metal connectors (SilTite™ mini unions from SGE). The preferred dimensions of the columns were determined by calibration using a standard of PACs dissolved in carbon disulphide.

The temperature for the first dimension column oven was programmed from 100° C. (5 minutes isothermal), followed by a ramp of 2° C./min to 350° C. (10 minutes isothermal). The temperature for the second dimension column oven was programmed from 150° C. (5 minutes isothermal), followed by a ramp of 2° C./min to 370° C. (25 minutes isothermal). The temperature of the hot pulse of the modulator was programmed from 150° C. (5 minutes isothermal), followed by a ramp of 2° C./min to 350° C. (35 minutes isothermal).

To prepare a deasphalted sample, 0.2 g of bituminuous material was weighed into a 100 ml flask, slightly heated if required. 2 ml of toluene was added to dissolve the sample. 60 ml of n-pentane was added and the flask was closed lightly with a cork. The flask was vibrated in an ultrasonic bath for 5 minutes, and then left to precipitate for 30 minutes.

A filter was placed in a funnel, a bottle was placed under the funnel and the pentane suspension was filtered through the filter paper, keeping the funnel covered in order to minimise evaporation of the pentane. The filter, flask and funnel were washed with 30 ml of n-pentane.

The bottle was placed in a water bath at about 45° C. and the pentane was evaporated with a gentle stream of nitrogen, providing the sample of deasphalted bituminous material.

To deasphalted bituminous materials were dissolved in the smallest quantity necessary of cyclohexane (this was typically about 2 ml).

The dissolved samples were injected into the PTV using a syringe equipped with a metal plunger. The liner of the PTV contained quartz wool up to 1.5 cm from the top of the liner and the syringe touched the quartz wool when the sample was introduced. The temperature of the PTV was programmed from 40° C. (0.0 minutes isothermal), followed by a ramp of 720° C./min to 300° C. (5 minutes isothermal). After finishing this temperature program, the PTV was cooled down at a ramp of 720° C./min to 125° C. (135 minutes waiting for the end of the run isothermal). A head pressure of 250 kPa (helium) was applied and the PTV was operated in split mode. The split flow was 20 ml/min.

The FID signal was acquired by an EZChrom Elite chromatography data system. MatLab version 6.5 was used for conversion of the linear signal into two-dimensional data matrices. GCxGC data was processed with in-house developed software (Mispelaar et al, *Journal of Chromatography A*, 1019 (2003) 15-29).

FIG. 1 shows a greyscale plot from the chromatographic analysis. The x axis is the first dimension retention time and the y axis is the second dimension retention time. The white dots visible on the diagonal represent different PACs. The least polar PACs (i.e. the monoaromatics) are found towards the bottom of the plot, and as the polarity increases (i.e. as the number of aromatic rings increases) the position on the plot moves upwards. The unsubstituted PACs are found towards the left hand side of the plot, and as the substitution (and boiling point) increases the position on the plot moves to the right hand side. The quantity of the different PACs is represented by the intensity of the dots. (In practice these plots are represented as false colour plots rather than greyscale plots.)

Figure 2:
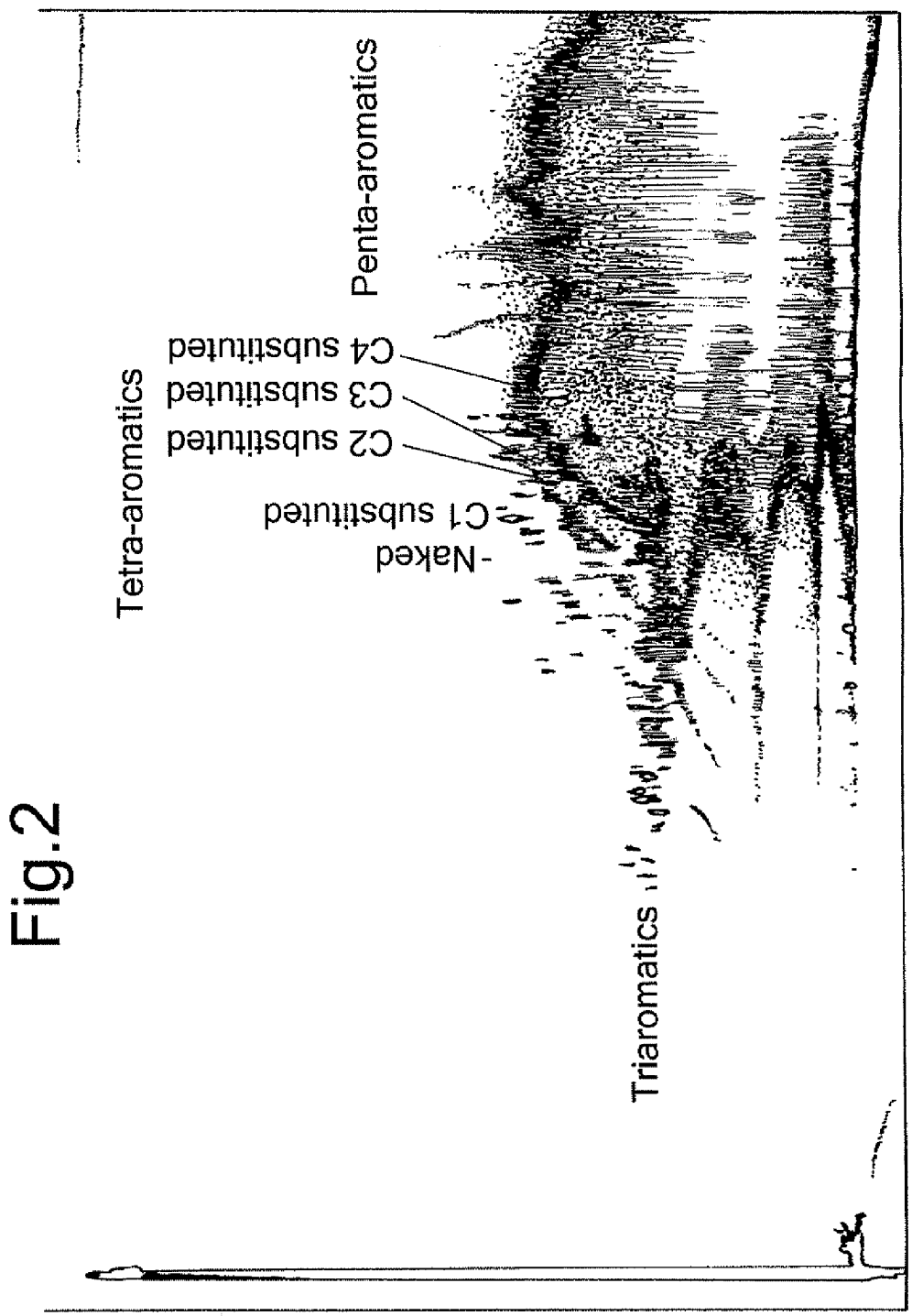

FIG. 2 shows a greyscale plot from the chromatographic analysis. A peak area of identified 4-aromatic ring PACs is shown. These compounds are considered to reflect the mutagenic tendency of a bituminous material. The compounds are separated according to the number of group substitutions which increases the molecular mass of the compounds and modifies their polarity.

What is claimed is:

1. A method of analysing the hydrocarbon compounds in a bituminous material by means of comprehensive multi-dimensional gas chromatography, wherein the method comprises the steps of;
    a) deasphalting a sample of the bituminous material, thereby providing a deasphalted sample;
    b) adding a solvent to the deasphalted sample, thereby providing a dissolved sample;
    c) using a programmed temperature vaporiser to inject the dissolved sample into a first capillary column, wherein the first capillary column comprises a non-polar stationary phase, thereby providing a first separated stream that emerges from the first capillary column;
    d) subjecting the first separated stream to a thermal modulation, thereby providing a thermally modulated stream;
    e) supplying the thermally modulated stream to a second column comprising a polar stationary phase, thereby providing a second separated stream that emerges from the second capillary column; and
    f) analysing the components in the second separated stream.

2. A method according to claim 1, wherein in step (a), pentane is used to deasphalt the sample of the bituminous material.

3. A method according to claim 2, wherein the solvent in step (b) is carbon disulphide.

4. A method according to claim 2, wherein in step (c), the programmed temperature vaporiser is used in a split mode.

5. A method according to claim 2, wherein the first capillary column comprises a dimethyl-polysiloxane stationary phase.

6. A method according to claim 2, wherein the thermal modulation is carried out using a cryogenic modulator.

7. A method according to claim 1, wherein the solvent in step (b) is carbon disulphide.

8. A method according to claim 7, wherein in step (c), the programmed temperature vaporiser is used in a split mode.

9. A method according to claim 7, wherein the first capillary column comprises a dimethyl-polysiloxane stationary phase.

10. A method according to claim 7, wherein the thermal modulation is carried out using a cryogenic modulator.

11. A method according to claim 1, wherein in step (c), the programmed temperature vaporiser is used in a split mode.

12. A method according to claim 11, wherein the first capillary column comprises a dimethyl-polysiloxane stationary phase.

13. A method according to claim 11, wherein the thermal modulation is carried out using a cryogenic modulator.

14. A method according to claim 1, wherein the first capillary column comprises a dimethyl-polysiloxane stationary phase.

15. A method according to claim 14, wherein the thermal modulation is carried out using a cryogenic modulator.

16. A method according to claim 1, wherein the thermal modulation is carried out using a cryogenic modulator.

17. A method according to claim 1, wherein the second capillary column comprises a 50% phenyl (equivalent) polysilphenylene-siloxane stationary phase.

18. A method according to claim 1, wherein metal connectors are used to connect the columns.

19. A method according to claim 1, further comprising: providing a chromatogram of the measured quantity of polycyclic aromatic compounds (PACs) in the bituminous material; and analyzing the chromatogram to determine the concentration of PACs.

20. A method according to claim 19, further comprising: determining the mutagenic tendency of the bituminous material using the measured quantity of polycyclic aromatic compounds (PACs) of the butimen material.

* * * * *